(12) United States Patent
Williams

(10) Patent No.: US 12,403,283 B2
(45) Date of Patent: *Sep. 2, 2025

(54) CENTRAL LINE CAP CARE KIT AND METHODS OF USING THE SAME

(71) Applicant: Carol E. Williams, Mint Hill, NC (US)

(72) Inventor: Carol E. Williams, Mint Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/423,880

(22) Filed: Jan. 26, 2024

(65) Prior Publication Data
US 2024/0173517 A1 May 30, 2024

Related U.S. Application Data

(60) Continuation of application No. 17/080,940, filed on Oct. 27, 2020, now Pat. No. 11,890,426, which is a division of application No. 15/975,127, filed on May 9, 2018, now Pat. No. 10,850,063.

(60) Provisional application No. 62/616,476, filed on Jan. 12, 2018, provisional application No. 62/503,503, filed on May 9, 2017.

(51) Int. Cl.
*A61M 25/00* (2006.01)
*A61M 39/08* (2006.01)
*A61M 25/01* (2006.01)
*B65D 85/08* (2006.01)

(52) U.S. Cl.
CPC ...... *A61M 25/002* (2013.01); *A61M 25/0097* (2013.01); *A61M 39/08* (2013.01); *A61M 2025/0019* (2013.01); *A61M 25/01* (2013.01); *B65D 85/08* (2013.01)

(58) Field of Classification Search
CPC .................. A61M 25/0097; A61M 25/002
See application file for complete search history.

(56) References Cited

U.S. PATENT DOCUMENTS

| | | | |
|---|---|---|---|
| 2002/0108614 A1 | 8/2002 | Schultz | A61M 16/0486 128/207.14 |
| 2005/0026275 A1 | 2/2005 | Bahoric | C12M 45/02 435/287.1 |
| 2005/0038374 A1 | 2/2005 | Williams | A61M 1/784 604/20 |
| 2009/0236259 A1 | 9/2009 | Hicks | A61B 50/30 206/570 |
| 2016/0228676 A1 | 8/2016 | Glithero | A61B 90/94 |

*Primary Examiner* — Kevin Joyner
(74) *Attorney, Agent, or Firm* — Stanek Lemon Crouse & Meeks, PA

(57) ABSTRACT

The present invention relates to a method of replacing a central line cap to a catheter, and a kit for central line cap care and replacement.

9 Claims, 2 Drawing Sheets

CENTRAL LINE CAP CARE KIT AND METHODS OF USING THE SAME

CROSS-REFERENCE TO RELATED APPLICATIONS

This application is a continuation of U.S. patent application Ser. No. 17/080,940; Filed Oct. 27, 2020, which divisional of U.S. patent application Ser. No. 15/975,127 filed May 9, 2018 (now U.S. Pat. No. 10,850,063), which claims priority to and the benefit of U.S. Patent Application Ser. No. 62/503,503, filed May 9, 2017, and U.S. Patent Application Ser. No. 62/616,476, filed Jan. 12, 2018, the disclosures of which are hereby incorporated by reference in their entireties.

FIELD OF THE INVENTION

The present invention relates to a kit for changing the cap on the hub of a central line catheter, and method for using the kit in changing the cap on the hub of a central line catheter in inpatient, outpatient, and/or at home settings.

BACKGROUND OF THE INVENTION

Central line-associated bloodstream infections (CLABSIs) are an ongoing concern with patients requiring a central line or central venous catheter (CVC). A central line is a catheter (tube) that is often placed in a large vein in, for example, the neck, chest or groin of a patient to provide medications or fluids or to collect blood for medical tests. Central lines are frequently used in intensive care units, and on cancer patients receiving chemotherapy both in and out patients. These central line catheters can in instances remain in place for weeks or months. As a result, central lines can be a potential source of serious infection. According to the Center for Disease Control and Prevention (CDC), about 41,000 bloodstream infections affect hospital patients with central lines each year, of which up to 1 in 4 will die as a result thereof. CLABSIs result in thousands of deaths each year and billions of dollars in added costs to the U.S. healthcare system.

A central line-associated bloodstream infection (CLABSI) is a serious infection that occurs when germs, such as bacteria or viruses, enter the bloodstream through contamination of the central line. Healthcare providers should follow a strict protocol when inserting the line to make sure the line remains sterile and a CLABSI does not occur. In addition to inserting the central line properly, healthcare providers should use stringent infection control practices each time the line is checked or the dressing surrounding the catheter is changed. Although progress has been made through the years to minimize the risk of CLABSIs, and guidelines have been set forth by the CDC for the prevention of intravascular catheter-related infections (O'Grady et al. (2011) Guidelines for the Prevention of Intravascular Catheter-Related Infections, 2011 <https://www.cdc.gov/hicpac/pdf/guidelines/bsi-guidelines-2011.pdf>) there still exists a need to develop improved products and methods for further reducing the risk of developing CLABSIs, such as, for example, improved products and methods involved in changing a cap to a central line, particularly in view of the increasing prevalence of antibiotic resistant bacteria, such as, for example, methicillin-resistant *Staphylococcus aureus* (MRSA), vancomycin-resistant *Enterococcus* (VRE) and carbapenem-resistant Enterobacteriaceae (CRE).

SUMMARY OF THE INVENTION

Provided herein are methods for changing a central line cap, and central line cap care kits. As such, according to an aspect of the invention, provided is a method of changing a central line cap of a catheter of a patient comprising: providing a mask and head cover for caregiver and patient, hand sanitizer, a plurality of sterile gloves, a plurality of sterile antiseptic swabs, sterile forceps, a sterile towel, a plurality of sterile gauze swabs, at least one pre-filled sterile flushing syringe comprising a physiologically appropriate injection solution, such as an isotonic injection solution, and a sterile field, wherein the caregiver performs the steps of: conducting hand hygiene; closing a clamp on the catheter or ensuring the clamp on the catheter is closed; having the caregiver and patient each don a head cover and a mask; conducting hand hygiene comprising using hand sanitizer; donning a first pair of sterile gloves; evacuating air from the sterile flushing syringe, attaching a new catheter cap to the sterile flushing syringe and filling the new catheter cap with the physiologically appropriate injection solution; setting the flushing syringe with the attached new catheter cap on the sterile field; wiping down/cleaning an old catheter cap and tubing of the central line leading into the old catheter cap with a sterile antiseptic swab; spreading the sterile towel, with the sterile forceps, under the cleaned old catheter cap and central line; removing the first pair of sterile gloves; donning a second pair of sterile gloves; removing the old catheter cap from the hub of the central line catheter using a plurality of sterile gauze swabs to assist with removing the old catheter cap; cleaning the central line catheter hub with a sterile antiseptic swab in order to clean the central line and allowing the central line to dry; attaching the new catheter cap to the end of the hub of the central line catheter; opening the clamp on the catheter; flushing the catheter, for example, according to the institution's protocol; closing the clamp on the catheter; and removing the flushing syringe from the new catheter cap, wherein the plurality of sterile antiseptic swabs, the sterile forceps, the sterile towel, the plurality of sterile gauze swabs, the pre-filled sterile flushing syringe or syringes comprising a physiologically appropriate injection solution and the sterile field are sterile components and/or provided in a sterile package or environment.

According to another aspect of the invention, provided is a cap care kit for a central line cap of a catheter comprising: a plurality of masks and head covers; hand sanitizer; a plurality of sterile gloves; a plurality of sterile antiseptic swabs; a sterile towel; sterile forceps; a plurality of gauze swabs; a plurality of pre-filled sterile syringes comprising a physiologically appropriate injection solution; and a sterile field.

DETAILED DESCRIPTION

Figure 1:
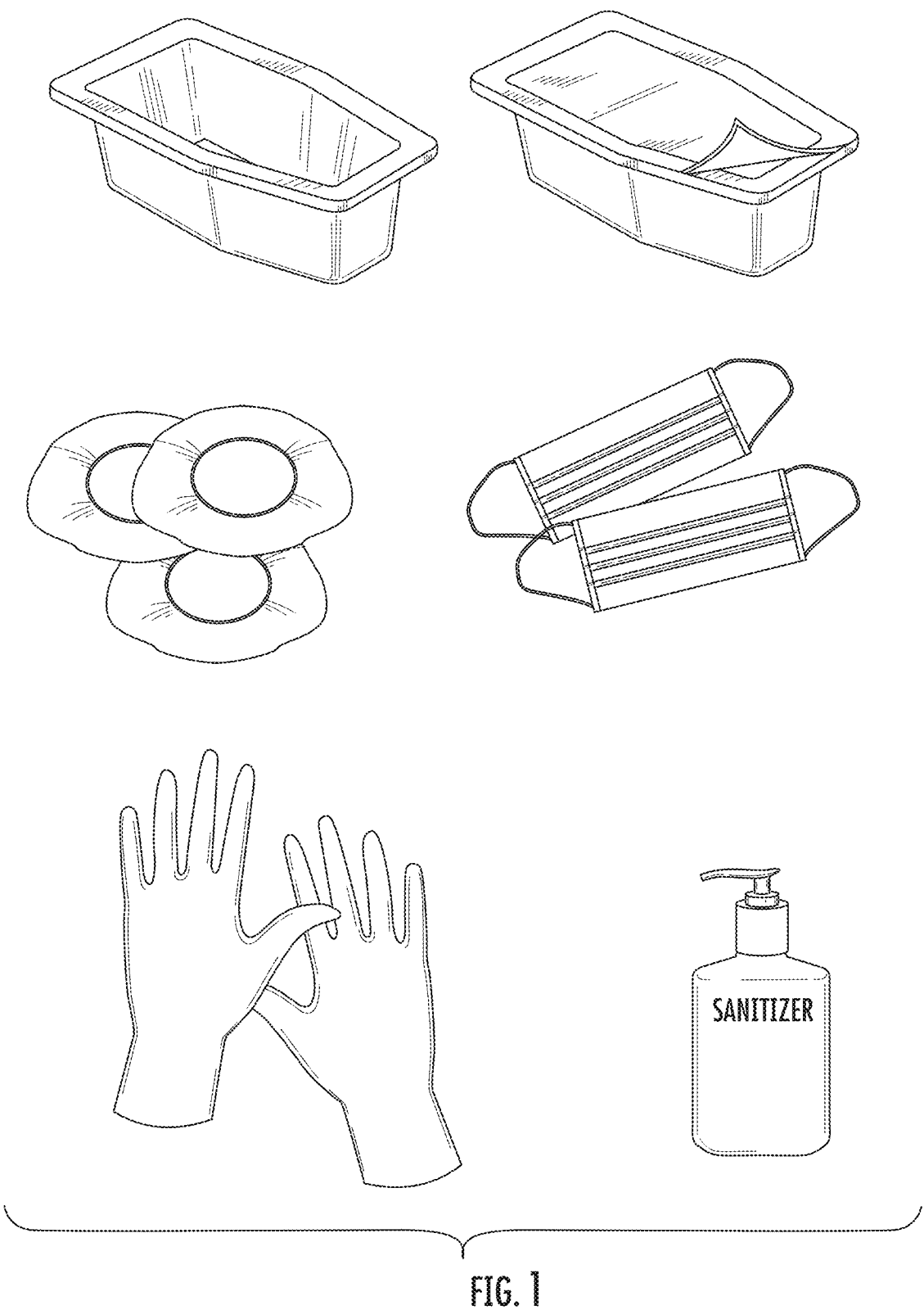
FIG. 1 depicts an example of kit components for central line cap care/replacement according to some embodiments of the invention. This embodiment may form an individual kit, a layer of a multilayered kit or the components of this kit may be combined with the kit components depicted in FIG. 2.

The invention will now be described more fully hereinafter. The invention, however, may be embodied in many different forms and should not be construed as limited to the exemplary embodiments as set forth herein. Rather, these embodiments are provided so that the disclosures will be thorough and complete, and will fully convey the scope of the invention to one of ordinary skill in the art.

As used herein, "a," "an" or "the" can mean one or more than one. Also as used herein, "and/or" refers to and encompasses any and all possible combinations of one or more of the associated listed items, as well as the lack of combinations when interpreted in the alternative ("or").

As used herein, "sterile" refers to free or essentially free of microorganisms. In a sterile environment, the chances of contamination by pathogenic organisms are reduced or eliminated.

As used herein, "essentially free" refers to 85%, 86%, 87%, 88%, 89%, 90%, 91%, 92%, 93%, 94%, 95%, 96%, 97%, 98%, 99%, 99.9% or 100% free.

As used herein, "hand sanitizer" or "hand sanitizing composition" refers to a substance used for or capable of cleaning the hands (or a surface in need thereof) so that they are free or essentially free of microorganisms, and examples include, soap (and water), alcohol, benzalkonium chloride, triclosan, povidone, iodine and combinations thereof.

As used herein, "pathogenic" or "microorganism" refer to bacteria, viruses, fungi and the like that can cause infection and/or disease.

As used herein, "towel" refers to a material such as a cloth or paper that may have a plastic backing, of any dimension suitable for the desired purpose that can be used as a surface or placed on an existing surface.

As used herein, "disinfecting" refers to microstatic or microbicidal action against a microorganism.

As used herein, "swab" refers to an absorbent piece of material that can be used for cleaning as described herein.

As used herein, "sterile packaging" refers to a sterile package that houses components and may provide a sterile or aseptic environment. These may be in the form of a "peel package" or "peel pack" or organizing trays that may include associated coverings or containments such as plastic, paper, metal or foam.

As used herein, "patient" refers to a subject. In particular embodiments, the subject is a human; however, a subject, and thus, a patient with respect to this invention can include an animal subject, particularly mammalian subjects such as canines, felines, bovines, caprines, equines, ovines, porcines, rodents (e.g. rats and mice), lagomorphs, primates (including non-human primates), etc., for veterinary medicine or pharmaceutical drug development purposes.

The subject or patient may be male, female or transgender and may be of any race or ethnicity, including, but not limited to, Caucasian, African-American, African, Asian, Hispanic, Indian, etc. The subjects may be of any age, including newborn, neonate, infant, child, adolescent, adult, and geriatric. In some embodiments, the subject is suffering from an infectious disease, cancer, a critical illness or need intensive care.

As used herein, "kit" refers to an assembly of components packaged together with optional instructions regarding how to use the components of the kit. According to embodiments of the present invention, the kits may include all components of the elements described herein for caring for a cap for a central line catheter of a patient, or a subset of the elements in any combination. That is, the kit may optionally include some of the following, but not necessarily all of a head cover, mask, hand sanitizer, gloves, syringe(s) including pre-filled syringes, swab, gauze, alcohol swab, forceps, sterile towel, and disposable sterile surface.

Embodiments of the present invention include methods for caring for a cap for a central line catheter of a patient, and more particularly a human patient. In some embodiments, care for a cap for a central line catheter includes replacing a cap for a central line catheter, for example, a cap that is presently covering the lumen of the central line, with a new cap. The frequency for replacing a central line cap is not particularly limited. For example, the central line cap may be changed once every 7 days, or once every week. Nevertheless, the frequency of replacing the central line cap may be varied as would be appreciated by one of ordinary skill in the art, for example, every other day, three days (72 hours), four days, five days, six days, seven days (1 week), eight days, nine days or 10 days. It would also be appreciated by one of ordinary skill in the art that the central line cap may also be replaced should the cap become contaminated or soiled or suspected of being contaminated or soiled, or after a blood draw, or administration of chemotherapy, or administration of a blood product, such as, whole blood, plasma, or platelets, regardless of the previously selected frequency for replacing the central line cap.

The method of changing the central line cap may include, for example, several components that may be provided in, for example, a kit for replacing a central line cap. In some embodiments, the kit may provide: at least one mask and at least one head cover for a caregiver and/or a patient; hand sanitizer; at least one pair of sterile gloves; at least one sterile antiseptic swab; at least one set of sterile forceps; at least one sterile towel, at least one sterile gauze swab; at least one pre-filled sterile flushing syringe including a physiological solution such as an isotonic solution, for example, a 0.9% sodium chloride, or normal saline, injection solution; and a sterile field. The site at which the method of the invention may take place is not particularly limited. For example, the method may take place in an inpatient setting, for example, at a hospital in which the patient has been admitted, in an outpatient setting, for example, at a clinic in which the patient does not stay overnight for the procedure, an urgent care setting or even at the home/residence of the patient.

Prior to proceeding with steps for changing the central line cap, in some embodiments, the method includes the caregiver conducting hand hygiene, which may include, for example washing of hands with soap and water, and/or optionally using conventional lotion, gel or foam hand sanitizer according to procedures that would be appreciated by one of ordinary skill in the art, for example, according to institutional protocols for conducting hand hygiene. In addition, prior to proceeding with the method, the caregiver may close a clamp to the central line, or ensure that the clamp to the central line is closed, in any manner or procedure as would be appreciated by one of ordinary skill in the art.

In some embodiments, the method includes both the caregiver and the patient donning or wearing both a mask, for example, but not limited to, an operating room (O/R) mask, and a head cover, for example, but not limited to, O/R head covers, in order to prevent contamination of the central line, by for example, but not limited to, breathing on the central line. Should any additional individuals be present while the central line cap is being changed, these individuals may also don or wear a mask and/or a head cover during the procedure, preferably both. The caregiver, patient and/or additional individuals present may also wear and change gloves during practice of the methods of the present invention.

In some embodiments, the method may include the caregiver using hand sanitizer and waiting for hands to dry following the donning of the head cover and mask. This may be followed by the donning of a first pair of sterile gloves prior to proceeding with changing the central line cap of the catheter.

The steps of changing the central line cap may include attaching a new catheter cap onto a sterile flushing syringe. The nature of the catheter cap is not particularly limited, and the catheter cap used in the process may be of any variety available to one of ordinary skill in the art. The nature, for example, the size or volume, of the sterile flushing syringe is also not particularly limited. However, in some embodiments, the sterile flushing syringe may be a 10 ml syringe that is pre-filled with an isotonic solution, for example, a 0.9% saline (sodium chloride), or normal saline, solution, as would be appreciated by one of ordinary skill in the art. In some embodiments, the isotonic solution may comprise heparin, for example, a heparin saline flushing solution. The sterile flushing syringe may then be purged of air by, for example, holding the sterile flushing syringe with the cap attached straight up and the plunger of the syringe pointing toward the floor, tapping the syringe so that any air bubbles rise to the top of the syringe, and pushing the plunger up to force out any air in the syringe. The new central line cap may now be attached and the new central line cap may now be filled with the flushing solution, such as 0.9% saline as described above. In the alternative, the new central line cap may be attached to the sterile flushing syringe, and then both the syringe purged of air and the new central line cap filled with flushing solution by inverting the syringe with attached new central line cap, tapping the syringe to cause air bubbles to rise to the top of the syringe, and forcing out any air in the syringe and new central line cap. In some embodiments, the sterile flushing syringe may comprise a LUER-SLIP™ connector, or a LUER-LOK™ threaded connector, to secure the new central line cap thereto. The amount of flushing solution such as 0.9% saline in the syringe after forcing air out may be, for example, at the 5 ml, 6 ml, 7 ml, 8 ml, or 9 ml mark, or any volume within the range from about the 5 ml mark to about the 9 ml mark. The new central line cap is now primed to replace the old central line cap, and may be set aside prior to removal of the old central line cap and cleaning the lumen, also known as the hub, of the central line catheter.

In some embodiments, the primed new central line cap attached to the sterile flushing syringe may be set aside on a sterile field, which will be detailed later. According to a conventional method for changing a central line cap, neither sterile gloves, nor any gloves at all, are required, and the sterile flushing syringe with the new central line cap attached thereto may be set on a non-sterile surface, such as a table, so long as the tip of new central line cap in not touched, which may lead to additional potential sources of contamination in the method of changing the central line cap.

In some embodiments, prior to removal of the old central line cap, the old central line cap and tubing from the central line of the catheter leading into the central line cap may now be wiped down and/or cleaned. This method may be performed by, for example, holding the central line catheter in one hand, and cleaning the old central line cap and tubing leading into the cap with an antiseptic swab in the other hand. Following wiping down and cleaning, the antiseptic swab may be discarded, and, in some embodiments, a sterile towel may be laid under the central line of the catheter that has just been wiped and cleaned with, for example, the assistance of a sterile set of forceps. The forceps may be disposable, and can be discarded following setting of the sterile towel under the area of the central line of the catheter.

The nature of the antiseptic cleaning product such as a swab or wipe is not particularly limited and may be a sterile cleaning product selected from the group consisting of alcohol swabs and sterile sponges, including an antiseptic product, for example impregnated with an antiseptic product. In some embodiments, the cleaning product such as a swab, cloth, wipe, or sponge, may include any antiseptic that would be appreciated by one of ordinary skill in the art. For example, the antiseptic of the swab, cloth, sponge, wipe, etc. may include chlorhexidine, povidone, iodine, an iodophor, or alcohol. In some embodiments, the antiseptic cleaner is an alcohol swab including 70% isopropyl alcohol. In some embodiments, the antiseptic cleaner is chlorhexidine (such as SITE-SCRUB®).

Prior to removing the old central line cap and attaching the new central line cap to the hub of the central line, in some embodiments, the caregiver may discard the first pair of sterile gloves and don a second pair of sterile gloves. In some embodiments, after removing the first pair of sterile gloves and prior to the donning of the second pair of gloves, hand hygiene and/or use of hand sanitizer may be conducted.

The old catheter cap may now be removed/unscrewed from the hub of the central line and discarded. In some embodiments, removal of the old central line cap may be assisted by the use of one or more than one sterile gauze swabs. Following removal, the old catheter cap may be discarded, and the lumen or hub of the central line is scrubbed or cleaned with a sterile antiseptic swab, for example, a sterile alcohol swab including 70% isopropyl alcohol or an antiseptic cleaner including chlorhexidine, for at least 5 seconds according to procedures that would be appreciated by one of ordinary skill in the art. In some embodiments, the lumen or hub may be scrubbed for at least 5 seconds to about 15 seconds. Following scrubbing/cleaning, the lumen should not be permitted to touch anything, and the antiseptic swabs used in the scrubbing/cleaning of the lumen or hub of the central line may be discarded.

The new catheter cap may now be attached to the lumen or hub of the central line, and flushed with the pre-filled sterile flushing syringe following opening of the clamp on the catheter. The flushing procedure may be performed using any standard protocol as would be appreciated by one of ordinary skill in the art, for example, flushing the central line according to institutional protocols, such as is set forth in, for example, Brigham and Women's Hospital and the Dana-Farber Cancer Institute, "Changing Your Central Line Catheter Cap" (<http://www.dana-farber.org/uploadedFiles/Library/health-library/articles/changing-your-central-line-catheter-cap.pdf>). The clamp on the catheter may now be closed, and the flushing syringe removed from the new catheter cap. In some embodiments, an alcohol cap or cover, for example a CUROS® (3M™) disinfecting port protector, may be attached to the new central line cap after the flushing syringe has been removed.

The procedure as described herein exemplifies the changing of a central line cap for a single lumen central line. However, the procedure may be repeated if, for example, the central line includes a double lumen, such as, for example, a Hickman central line, in which more than one central line cap must be replaced. As such, in some embodiments, more than one pre-filled flushing syringe and more than one new central line cap may be provided, and optionally, more than one cap or cover may be provided, if more than one central line cap is in need of replacement. For example, following replacement of a first central line cap, a second new central line cap may be primed with a second pre-filled flushing syringe, and the steps for replacing a central line cap, such as described herein, may be performed in order to replace a second central line cap, such as with a double lumen Hickman central line catheter, or if a patient has more than one single lumen central line catheter.

In still other embodiments of the invention, provided is a kit for central line cap care, or for changing a central line cap of a catheter. The kit may include all of items or components required to carry out the method of the invention as described herein. For example, the kit may include: a plurality of masks and head covers; hand sanitizer; a plurality of sterile gloves; a plurality of sterile antiseptic swabs; a sterile towel; sterile forceps; a plurality of sterile gauze swabs; at least one pre-filled sterile flushing syringe comprising a saline (such as 0.9% sodium chloride) injection solution; and a sterile field. A new central line cap or a plurality of new central line caps may be provided separately or as part of the kit.

In some embodiments, the kit for central line cap care or changing a central line catheter cap may provide various individual items or components required to carry out the method of the invention as described herein in separate packs or packages. For example, one pack or package of the kit may include: a plurality, or at least two, head covers; a plurality, or at least two, masks (for both caregiver and patient); hand sanitizer; and a plurality, or at least two pairs of sterile gloves, and a second pack or package of the kit may include: a plurality of sterile antiseptic swabs; a sterile towel; sterile forceps, more particularly disposable sterile forceps; a plurality of sterile gauze swabs or pads; at least one, or a plurality, of pre-filled sterile flushing syringe; and a sterile field.

In some embodiments, the second package and the contents contained therein, as provided, are sterile, i.e., the second pack or package is a sterile pack or package. The nature of the sterile pack or package is not particularly limited, and may be of any form that may be appreciated by one of ordinary skill in the art. In some embodiments, the sterile pack or package may be a peel-pouch, a peel-pack, or peel-package. In some embodiments, the individual contents of the second pack or package, for example, the sterile antiseptic swabs, the sterile towel, sterile forceps, sterile gauze swabs or pads; the pre-filled sterile flushing syringe(s) and/or the sterile field, may be provided in sterile peel-pouches, sterile peel-packs or sterile peel-packages within the second pack or package.

The second pack or package may include a sterile field. The nature of the sterile field is not particularly limited, so long as the pre-filled sterile flushing syringe(s) with a new central line cap attached thereto may be set thereon. In some embodiments, the sterile field may be a wrapper for the contents of the second package. In some other embodiments, the sterile field may be the container or a portion of the container, in which the contents of the second pack or package are provided. The container may include separators or dividers in which the contents are disposed, or to provide an area upon which a new central line cap or caps, or the pre-filled sterile flushing syringe(s) with a new central line cap attached thereto, may be set thereon when changing a central line catheter cap.

In some embodiments, the individual contents of the first pack or package, for example, the head covers, the masks, the hand sanitizer, and/or the sterile gloves, may be provided in sterile peel-pouches, sterile peel-packs or sterile peel-packages.

Figure 2:
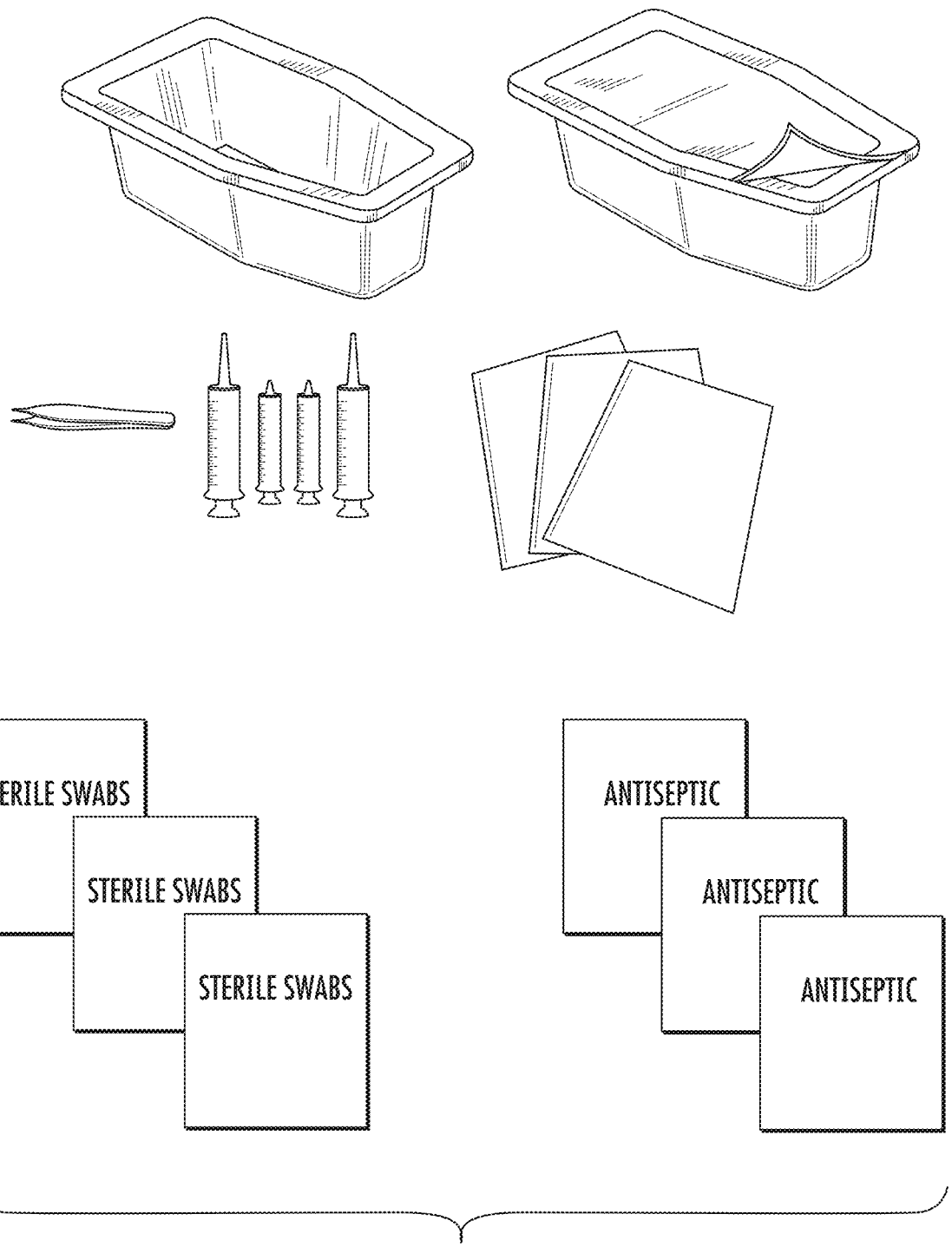
FIG. 2 depicts a further example of kit components for central line cap care/replacement according to some embodiments of the invention. This embodiment may form an individual kit, a layer of a multilayered kit or the components of this kit may be combined with the kit components depicted in FIG. 1.

The manner in which the two packs or packages including the contents of the kit of the invention are disposed is not particularly limited. In some embodiments, the first and second packs or packages of the kit of the present invention may be provided separately or combined. In other embodiments, the first and second packs or packages of the kit of the present invention may be provided together as a single unit, in which the first pack or package can be provided as a first or upper "layer," and the second pack or package, which in some embodiments, is sterile, can be provided as a second or lower layer of the kit. Exemplary layers of the first pack and the second pack of an embodiment of the kit are depicted in FIGS. 1 and 2. FIG. 1 shows the contents of the first or upper pack/layer of the kit, including head covers, masks, hand sanitizer and gloves, whereas FIG. 2 shows the contents of the second or lower pack/layer of the kit, including the plurality of sterile antiseptic swabs, the sterile towel, sterile forceps, the plurality of sterile gauze swabs or pads, the at least one or a plurality of pre-filled sterile flushing syringes. In some embodiments, the container and the contents of the second pack or package are sterile. The second pack or package, for example, the container, such as is depicted in FIG. 2, may serve as, in some embodiments, the sterile field on which a new central line cap that has been attached to a pre-filled sterile flushing syringe may be set prior to attaching the new central line cap to the lumen/hub of the central line. In other embodiments, the sterile second pack or package may include a sterile wrapper for the contents therein, which may serve as the sterile field.

The sterile field is provided so as to further reduce the risk of contamination, which may lead to a CLABSI, during a central line cap change procedure by providing an aseptic area on which components used in the central line cap change procedure may be set. The sterile field may also facilitate use of the kit for changing a central line cap in environments other than in a hospital, i.e., inpatient, or a clinic, i.e., outpatient setting. For example, the kit may facilitate changing a central line cap at the home/residence of a patient (i.e., where the patient is staying outside of a hospital or clinical setting), while reducing the risk of contamination and infection in such a setting.

In yet other embodiments, the kit, and the contents of the kit, can be latex-free so as to avoid potential latex sensitivity or allergies of either the patient or the caregiver. The kit may also optionally include, for example, alcohol covers for the central line caps, which may be provided separately from the first and second pack or packages of the kit.

According to further embodiments of the invention, the method for changing a central line cap of a catheter of a patient, as set forth herein, may be performed using a kit, for example, a cap care kit, such as is set forth herein. In some embodiments, the method of for changing a central line cap for a catheter may include providing a plurality of masks and head covers for caregiver and patient, hand sanitizer, a plurality of sterile gloves, a plurality of sterile alcohol swabs, sterile forceps, a sterile towel, a plurality of sterile gauze swabs, at least one pre-filled sterile flushing syringe comprising a saline (such as 0.9% sodium chloride) injection solution and a sterile field in a kit, such as is set forth herein. The provided kit and components therein may be accessed or opened, for example, after the caregiver has conducted hand hygiene and has closed or ensured that the clamp on the catheter or ensuring the clamp on the catheter is closed.

Example

Changing of Central Line Cap

The following example has been included to provide guidance to one of ordinary skill in the art for practicing representative embodiments of the presently disclosed subject matter. In light of the present disclosure and the general level of skill in the art, those of skill can appreciate that the following example is intended to be exemplary only and that numerous changes, modifications, and alterations can be employed without departing from the scope of the presently disclosed subject matter.

At least some, if not all, of the following components are included as an assembly of components, which may be included as part of a sterile environment:
Head cover
Mask
Hand sanitizer
Plurality of sterile gloves
Sterile forceps,
Sterile towel,
Sterile gauze
Sterile pre-filled flushing syringe—comprising of sodium chloride (e.g., 0.9% sodium chloride injection 10 mls) (at least one)
Sterile field
Plurality of sterile cleaning products (e.g., alcohol swabs, sterile sponges, which can be impregnated with an antiseptic product such as chlorhexidine (CHG) and povidone—iodine At least some, if not all, of the following steps may be carried out in the exemplary procedure:
(a) Conducting hand hygiene
(b) Explain the procedure to the patient and or family member
(c) Closing the clamp on the catheter or ensure that it is closed
(d) Open the kit
(e) Remove head cover, mask, hand sanitizer and $1^{st}$ pair of sterile gloves from a $1^{st}$ layer of kit (FIG. 1)
(f) Have care giver (and patient each) don head cover and mask
(g) Open the $2^{nd}$ layer of the kit (FIG. 2)
(h) Peel open the sterile cap into the kit
(i) Care giver use hand sanitizer—allow to dry
(j) Don the $1^{st}$ pair of sterile gloves
(k) Evacuate air from flushing syringe
(l) Attach the new sterile cap to the flushing syringe, filling it with a physiological solution such as sodium chloride
(m) Set the flushing syringe with the attached new catheter cap on the sterile field
(n) Wipe down and clean the used catheter cap and section of tubing leading to the cap with antiseptic swab. Allow to dry
(o) Use sterile forceps to spread sterile towel under the cleaned used catheter cap and central line
(p) Remove $1^{st}$ pair of sterile gloves
(q) Don $2^{nd}$ pair of sterile gloves
(r) Remove the used cap from the central line with the assistance of sterile gauze if necessary and discard same
(s) Clean the hub of catheter with antiseptic swab (as per institution's protocol)—using friction and twisting motion (allow to dry)
(t) Attach the new cap with the flush syringe to the hub of the catheter
(u) Open the clamp on the catheter
(v) Verify blood return
(w) Flush catheter (as per institution's protocol)
(x) Close clamp on catheter
(y) Remove flushing syringe from the new catheter cap
(z) Repeat above for all other lumens. Using new wipes, flushing syringes, towel and gloves as needed
Optional post-procedure protocol includes the following:
Discard supplies
Remove gloves and hat
Wash hands with soap and water In general, the invention provides methods and kits that allow the sterile changing of a cap of a central line of a catheter. Components as needed to achieve the same are provided in sterile packaging in order to maintain a sterile environment. Thus, the components can be provided for convenience within a sterile package altogether or in multiple sterile packages to comprise a kit. Moreover, those components that can be pre-purchased as sterile can be provided separately and combined post sterilization with components that require sterilization after purchase in order to provide sterile components and a sterile environment for changing, replacing or establishing the cap of a central line of a catheter.

While the present invention has been shown and described with reference to some embodiments thereof using specific terms, the embodiments and terms have merely been used to explain the present invention and should not be construed as limiting the scope of the invention as defined by the claims. Therefore, the scope of the invention is not defined by the detailed description, but by the appended claims, and all differences within the scope will construed as being included in the invention.

That which is claimed is:

1. A cap care kit for a central line cap of a catheter consisting of:
a plurality of masks and head covers;
a plurality of sterile gloves;
sterile forceps;
a sterile towel;
a plurality of gauze swabs or pads;
at least one pre-filled sterile flushing syringe comprising a physiological injection solution;
a sterile field;
a plurality of sterile cleaning products selected from the group consisting of alcohol swabs and sterile sponges comprising an antiseptic product; and
at least one new central line catheter cap.

2. The cap care kit of claim 1, wherein the cap care kit is latex-free.

3. The cap care kit of claim 1, wherein the contents of the cap care kit are sterile.

4. A cap care kit for a central line cap of a catheter consisting of:
a plurality of masks and head covers;
hand sanitizer;
a plurality of sterile gloves;
a plurality of gauze swabs or pads; and
at least one pre-filled sterile flushing syringe comprising a physiological injection solution;
wherein the contents of the cap care kit are housed in a container wherein the container or a portion thereof is a sterile field.

5. The cap care kit of claim 4, wherein the container comprises a divider defining an area wherein the contents of the cap care kit are disposed after use.

6. The cap care kit of claim 4, wherein the container comprises a divider defining and area wherein a new central line cap and/or a sterile flushing syringe with a new central line cap attached thereto may be set thereon when changing a central line catheter cap that is in use.

7. The cap care kit of claim 4, wherein the plurality of masks and head covers, hand sanitizer, and the plurality of sterile gloves are provided in a first package, and the plurality of sterile alcohol swabs, the plurality of sterile cleaning products, the at least one pre-filled sterile flushing syringe are provided in a second package.

8. The cap care kit of claim 7, wherein the first and second packages of the kit comprise a single unit in which the first package comprises an upper layer and the second package comprises a lower layer of the kit.

9. A cap care kit for a central line cap of a catheter consisting of:
- at least one mask;
- at least one head cover;
- a plurality of sterile gloves;
- a plurality of gauze swabs or pads; and
- at least one pre-filled sterile flushing syringe comprising a physiological injection solution;
- wherein the contents of the cap care kit are housed in a container wherein the container or a portion thereof is a sterile field.

* * * * *